United States Patent [19]

Blackburn

[11] Patent Number: 4,732,045

[45] Date of Patent: Mar. 22, 1988

[54] METHOD FOR RAPID ACOUSTIC EMISSION TESTING OF PRESSURE VESSELS

[75] Inventor: Philip R. Blackburn, Niagara Falls, N.Y.

[73] Assignee: Union Carbide Corporation, Danbury, Conn.

[21] Appl. No.: 15,984

[22] Filed: Feb. 18, 1987

[51] Int. Cl.⁴ .............................................. G01N 29/04
[52] U.S. Cl. ......................................... 73/801; 73/37; 73/587
[58] Field of Search ............................ 73/801, 587, 37

[56] References Cited

U.S. PATENT DOCUMENTS

| | | |
|---|---|---|
| 3,229,509 | 1/1966 | Darby. |
| 3,545,262 | 12/1970 | Steele et al. ...................... 73/801 X |
| 4,036,057 | 7/1977 | Morais ............................. 73/801 X |
| 4,468,965 | 9/1984 | Blackburn ........................... 73/587 |
| 4,577,487 | 3/1986 | Dooley ................................. 73/37 |

OTHER PUBLICATIONS

Harris, D. O. et al, *Verification of Structural Integrity of Pressure Vessels by Acoustic Emission and Periodic Proof Testing*, Technical Report DRC-71-2 Dunegan Corp., pp. 1-14, May 1971.

*Primary Examiner*—Stewart J. Levy
*Assistant Examiner*—Joseph W. Roskos
*Attorney, Agent, or Firm*—Stanley Ktorides

[57] ABSTRACT

A method for the rapid acoustic emission testing of pressure vessels wherein the flow rate of the pressurizing fluid is increased while maintaining the velocity of the pressurizing fluid, as it enters the pressure vessel, below the velocity which would cause the generation of flow noise.

24 Claims, 1 Drawing Figure

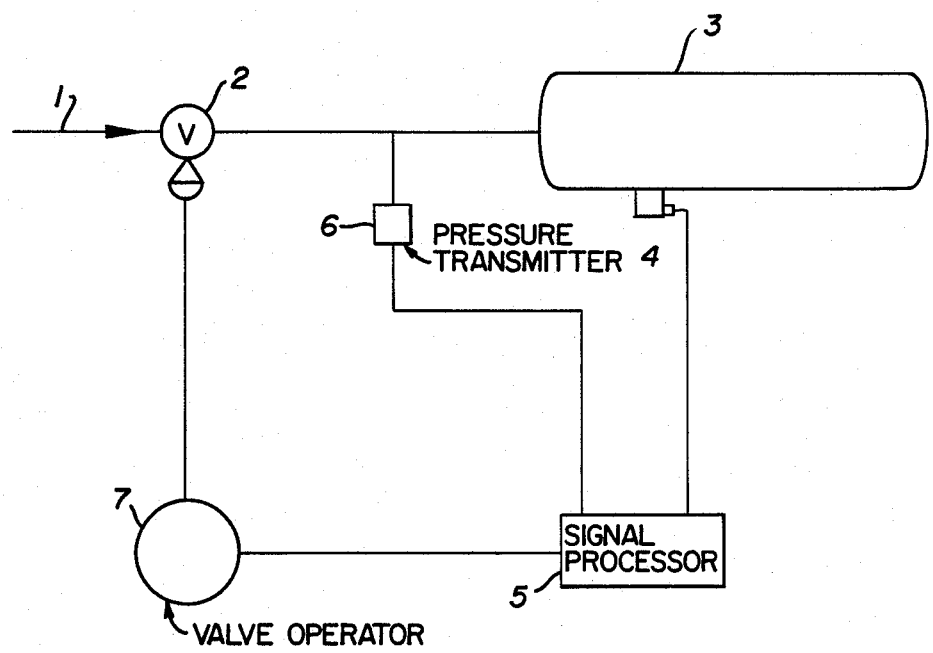

4,732,045

METHOD FOR RAPID ACOUSTIC EMISSION TESTING OF PRESSURE VESSELS

TECHNICAL FIELD

This invention relates to the testing of pressure vessels by acoustic emission in order to determine the structural integrity of pressure vessel walls, and is an improvement whereby the testing can be carried out faster without a decrease in the accuracy of the test results.

BACKGROUND ART

Acoustic emission testing is a technique for accessing structural integrity. The presence of flaws in pressure vessels can be detected with this technique. Acoustic sensors are affixed to the pressure vessel wall, and are connected to a signal processor. When the vessel is pressurized, flaws will produce stress wave emission. The stress waves will propagate throughout the vessel and passage of stress waves will be detected by the sensors.

A problem associated with acoustic emission testing is the generation of acoustic emission events caused, not by structural flaws within the vessel, but by the action of pressurizing fluid. Secondary flows impinge upon the inside walls of the pressure vessel and may produce noise which affects the sensors. Such flow noise may produce acoustic emission data in addition to that produced by flaws. There are some conventional ways to eliminate flow noise but these conventional methods have severe disadvantages.

One way of addressing the flow noise problem is to pressurize the vessel to the target pressure at a low flow rate thus reducing or completely eliminating secondary flows and hence the noise problem. However this method is disadvantageous because of the consequent long time it takes to pressurize the vessel to the desired pressure. This time problem is especially severe when there are a large number of pressure vessels which must undergo testing.

Another way of addressing the flow noise problem is to set a high threshold on the acoustic emission signal processor so that the signals associated with secondary flows are below the threshold. This has the unfavorable result of the failure to record low amplitude structural emission.

It is therefore an object of this invention to provide a method for carrying out acoustic emission testing of a pressure vessel in an elapsed time faster than heretofore possible while reducing inaccuracy of test data due to flow noise from the pressurizing fluid and/or to a high threshold on the acoustic emission signal processor.

SUMMARY OF THE INVENTION

The above and other objects which will become apparent to one skilled in the art upon a reading of this disclosure are attained by the present invention one aspect of which is:

A method for carrying out acoustic emission testing of a pressure vessel comprising pressurizing the vessel to a target pressure by introducing pressurization fluid into the vessel while substantially continually increasing the pressurization fluid flowrate into the vessel and maintaining the pressurization fluid velocity substantially constant, so as to generate acoustic emission capable of being read by at least one acoustic emission sensor on the vessel.

Another aspect of the method of this invention is:

A method for carrying out acoustic emission testing of a pressure vessel comprising:

(a) pressurizing the vessel to an interim pressure less than the target pressure by introducing pressurization fluid into the vessel while the fluid velocity into the vessel decreases from the initial velocity to an interim velocity; and thereafter (b) pressurizing the vessel to the target pressure by passing pressurization fluid into the vessel while, at least once, increasing the pressurization fluid velocity, by increasing the pressurization fluid flow rate into the vessel, to exceed the interim velocity while maintaining the fluid velocity below the velocity which would cause flow noise, so as to generate acoustic emission capable of being read by at least one acoustic emission sensor on the vessel.

Still another aspect of the method of this invention is:

A method for carrying out acoustic emission testing of a pressure vessel comprising:

(a) pressurizing the vessel at an initial flow rate;

(b) increasing the flow rate to attain a high flow rate which, if decreased, causes the rate of acoustic emission to decrease;

(c) reducing the flow rate until no further decrease in the rate of acoustic emission occurs; and thereafter (d) pressurizing the vessel to a target pressure so as to generate acoustic emission capable of being read by at least one acoustic emission sensor on the vessel.

BRIEF DESCRIPTION OF THE DRAWING

The sole FIGURE is a simplified schematic diagram of one preferred arrangement which may be employed to carry out the method of this invention.

DETAILED DESCRIPTION

The method of this invention will be described in detail with reference to the FIGURE.

Referring now to the FIGURE, pressurizing fluid 1 is passed from a source through valve 2 and into pressure vessel 3 at an initial flow rate. The pressurizing fluid may be any suitable fluid. Preferably the pressurizing fluid is a gas such as nitrogen or air. It may be advantageous to employ the normal working fluid of the pressure vessel as the pressurizing fluid. The source of pressurizing fluid 1 is any convenient source such as a high pressure gas cylinder, a pipeline source, or a compressor.

The pressurizing fluid is throttled through valve 2 to pass into pressure vessel 3 at an initial flow rate. The initial flow rate will vary depending on the size and/or dimensions of the pressure vessel and piping; generally the initial flow rate will be within the range of from 1 to 10 standard cubic feet per minute (scfm).

Pressure vessel 3 may be any pressure vessel having a shell and an interior into which pressurizing fluid may flow. The method of this invention is particularly useful for testing steel cylinders used in the distribution of industrial gases such as gas storage cylinders and tube trailers.

Pressurizing fluid 1 passes into pressure vessel 3 at an initial velocity. The initial velocity will vary depending upon the initial flow rate and upon the size of the pressure vessel port through which the pressurization fluid is passed. The fluid velocity of importance is the pressurizing fluid velocity at the inlet port used to introduce the fluid into the vessel. Generally the initial velocity will be within the range of from 5 to 20 feet per second.

On the outer surface of pressure vessel 3 is at least one acoustic emission sensor 4. Acoustic emission sensors are well known to those skilled in the art and no further detailed description is necessary herein. Generally the acoustic emission sensors are piezoelectric transducers and are held against the pressure vessel wall with adhesive tape. A suitable acoustic coupling medium, e.g. stopcock grease, is used. Acoustic emission measured by the sensor(s) are sent as electric signals to signal processor 5 which usually includes an amplifier and a counter. The system also includes a preamplifier which may be separate or integrated with the sensor. This sensing and recording equipment is available commercially and those skilled in the art are familiar with the procurement and use of such equipment.

The interior of the pressure vessel 3 may initially be at any pressure; however generally the initial pressure within pressure vessel 3 is ambient pressure, i.e., zero pounds per square inch gauge (psig). As the pressurizing fluid passes into pressure vessel 3 at the initial flow rate, the pressure within vessel 3 increases. The pressure is read by pressure transmitter 6 and the reading is electrically passed to acoustic emission signal processor 5.

In a particularly preferred embodiment, the process of this invention comprises substantially continually increasing the flowrate of the pressurization fluid into the vessel so as to maintain the fluid velocity within the range of from substantially constant to plus or minus 25 percent. When the initial velocity is at or about the highest velocity which can be attained without causing flow noise, this particularly preferred embodiment will result in the carrying out of the acoustic emission test in the shortest elapsed time. In this particularly preferred embodiment valve operator 7 continually operates valve 2 so as to be increasing the flowrate into the vessel.

Equipment or control limitations may require that the method of this invention be carried out with one or more step increases in fluid flowrate rather than with a continuous flowrate increase. In this situation, the fluid velocity will decrease during each step as the pressure within the vessel increases. This embodiment of the method of this invention may be carried out as follows.

When the pressure within pressure vessel 3 has increased to an interim pressure and the fluid velocity has decreased from the initial velocity to an interim velocity, valve operator 7 activates valve 2 so as to increase the flow rate of the pressurizing fluid causing the fluid velocity to exceed the interim velocity. The pressurization fluid velocity is maintained below the velocity which would cause flow noise. Valve operator 7 may be a person or automatic computing means such as a microprocessor or programmed controller. The change in the flow rate may occur once during the testing of the pressure vessel, or it may occur more than once in a series of separate adjustments.

The pressurizing fluid passes into the vessel at the higher flow rate until the desired or target pressure is attained within the vessel. The target pressure may be any pressure suitable to enable an accurate acoustic emission test. Generally the target pressure is within the range of from 105 to 150 percent of the normal service pressure of the vessel.

As the pressurizing fluid passes into the pressure vessel to pressurize the vessel to the target pressure, pressure on the interior walls of the vessel causes acoustic emission events which are sensed by the acoustic emission sensor(s) and transmitted to signal processor 5 for recording. The resulting data can be interpreted to determine the structural integrity of the pressure vessel.

In either the continuous increase or stepped increase embodiment of this invention it is preferred that the initial velocity of the pressurization fluid be the highest possible without attaining flow noise. Thereafter the test is carried out while not exceeding this initial velocity. However, because the maximum velocity without causing flow noise is specific to each type of vessel and to each set of operating conditions, it is often difficult to know before the test what this maximum velocity is. In this situation the maximum velocity may be attained as follows.

The pressure vessel is pressurized at an initial flow rate and the rate is increased until it reaches a high rate which, if decreased, causes the rate of acoustic emission events to decrease. Acoustic emission events whose rate varies with the flow rate are generated by flow noise rather than by structural flaws. In this situation the valve operator, e.g. a person or a microprocessor, then decreases the flow rate until there is no further decrease in the rate of acoustic emission events. Acoustic emission events which occur at the reduced flow rate are related to structural phenomena. The pressure vessel is then pressurized to the desired or target pressure without exceeding the fluid velocity at the decreased flowrate while the flowrate itself is increased either continuously or in stages. In this way the vessel is pressurized at the highest velocity allowable without the generation of flow noise caused by secondary flows.

As indicated above, fluid velocity at the vessel port will decrease as pressure within the vessel increases. Most of the time, the flow rate will remain constant even though velocity at the vessel inlet decreases. Flow rate will depend only on the control valve opening and the supply pressure. This condition exists as long as flow through valve 2 is choked. With choked flow the gas velocity through valve 2 equals the speed of sound. This is the maximum velocity possible in such systems. Choked flow will persist until pressure within the vessel reaches approximately one-half the supply pressure. When this happens, flow rate starts to decrease when pressure within the vessel increases. It no longer remains constant. The gas velocity at the control valve is now sub-sonic.

The following example serves to further illustrate the method of this invention. It is presented for illustrative purposes and is not intended to be limiting.

EXAMPLE 1

The structural integrity of a gas storage cylinder having an internal volume of 1.98 cubic feet was tested by measuring acoustic emission employing an arrangement similar to that illustrated schematically in the FIGURE. The target pressure was 250 psig and the initial pressure within the cylinder was 0 psig. The pressurization fluid was gaseous nitrogen. An acoustic emission sensor with 150 kHz resonant frequency was attached to the outside of the cylinder. Signals from the sensor were filtered through a 100 to 300 kHz bandpass. The signal processor threshold was set at 40 decibels (referenced to 1 microvolt at the sensing element).

The pressurization fluid was passed into the gas storage cylinder at an initial flow rate of 2.6 scfm and at an initial velocity of about 11 feet per second so as to increase the pressure within the cylinder to an interim pressure of 60 psig. During this first pressurization step, as the pressure within the cylinder increased from 0 to 60 psig, the fluid velocity was decreased from the initial velocity to an interim velocity of about 2.2 feet per second. The pressurization fluid flow rate was then increased to 9.3 scfm while the pressurization fluid velocity was increased to about 7.9 feet per second. The cylinder was pressurized to the target pressure without any other increases in the fluid flowrate. Acoustic emission events were generated during the pressurization which were read by the sensor. None of the acoustic emission events were caused by flow noise. The total elapsed test time was 7.2 minutes.

For comparative purposes the following comparative example is reported.

A gas storage cylinder similar to that of Example 1 was tested for structural integrity using the same testing arrangement as that described in Example 1. Pressurization fluid was passed into the cylinder at an initial flow rate of 2.6 scfm which was the highest flow rate possible at the outset of pressurization before flow noise from secondary flows exceeded the signal processor threshold. The cylinder was pressurized to the target pressure of 250 psig to generate acoustic emission events free of flow noise. The total elapsed test time was 15.2 minutes.

It is thus demonstrated that the method of this invention enables, in the particular case reported, a reduction in the test time of 54 percent without contaminating test results with flow noise.

Now by the use of the method of this invention wherein pressurizing fluid flow rate is increased while maintaining pressurizing fluid velocity below the velocity which would cause flow noise, one can carry out acoustic emission testing of pressure vessels much more rapidly than was heretofore possible.

Although the method of this invention has been described in detail with reference to certain specific embodiments, it is recognized that there are other embodiments of the invention within the spirit and scope of the claims.

I claim:

1. A method for carrying out acoustic emission testing of a pressure vessel comprising pressurizing the vessel to a target pressure by introducing pressurization fluid into the vessel while substantially continually increasing the pressurization fluid flowrate into the vessel and maintaining the pressurization fluid velocity within plus or minus 25 percent, so as to generate acoustic emission capable of being read by at least one acoustic emission sensor on the vessel.

2. The method of claim 1 wherein the pressurization fluid is nitrogen.

3. The method of claim 1 wherein the pressurization fluid velocity is about the maximum velocity which can be attained without generating flow noise.

4. The method of claim 1 wherein the fluid velocity is within the range of from 5 to 20 feet per second.

5. The method of claim 1 wherein the target pressure is within the range of from 105 to 150 percent of the service pressure of the vessel.

6. The method of claim 1 wherein the pressure vessel is a gas storage cylinder.

7. The method of claim 1 wherein the pressure vessel is a tube trailer.

8. The method of claim 1 wherein the pressurization fluid velocity is maintained substantially constant while the pressurization fluid flowrate into the vessel is being continually increased.

9. A method for carrying out acoustic emission testing of a pressure vessel comprising:
   (a) pressurizing the vessel to an interim pressure less than the target pressure by introducing pressurization fluid into the vessel while the fluid velocity into the vessel decreases from the initial velocity to an interim velocity; and thereafter
   (b) pressurizing the vessel to the target pressure by passing pressurization fluid into the vessel while, at least once, increasing the pressurization fluid velocity, by increasing the pressurization fluid flow rate into the vessel, to exceed the interim velocity while maintaining the fluid velocity below the velocity which would cause flow noise, so as to generate acoustic emission capable of being read by at least one acoustic emission sensor on the vessel.

10. The method of claim 9 wherein the pressurization fluid is nitrogen.

11. The method of claim 9 wherein the fluid velocity is within the range of from 5 to 20 feet per second.

12. The method of claim 9 wherein the target pressure is within the range of from 105 to 150 percent of the service pressure of the vessel.

13. The method of claim 9 wherein the pressure vessel is a gas storage cylinder.

14. The method of claim 9 wherein the pressure vessel is a tube trailer.

15. The method of claim 9 wherein in step (b) the fluid flowrate is increased so as to exceed the fluid flowrate at the end of step (a).

16. A method for carrying out acoustic emission testing of a pressure vessel comprising:
   (a) pressurizing the vessel at an initial flow rate;
   (b) increasing the flow rate to attain a high flow rate which, if decreased, causes the rate of acoustic emission to decrease;
   (c) reducing the flow rate until no further decrease in the rate of acoustic emission occurs; and thereafter
   (d) pressurizing the vessel to a target pressure so as to generate acoustic emission capable of being read by at least one acoustic emission sensor on the vessel.

17. The method of claim 16 wherein step (d) is carried out by pressurizing the vessel to the target pressure by introducing pressurization fluid into the vessel while substantially continually increasing the pressurization fluid flowrate into the vessel and maintaining the pressurization fluid velocity substantially constant.

18. The method of claim 16 wherein step (d) is carried out by pressurizing the vessel to an interim pressure less than the target pressure by introducing pressurization fluid into the vessel while decreasing the fluid velocity into the vessel from the initial velocity to an interim velocity; and thereafter pressurizing the vessel to the target pressure by passing pressurization fluid into the vessel while, at least once, increasing the pressurization fluid velocity into the vessel to exceed the interim velocity while maintaining the fluid velocity at or below the velocity of the fluid at the reduced flowrate of step (c).

19. The method of claim 16 wherein step (d) is carried out by pressurizing the vessel to the target pressure by inroducing pressurization fluid into the vessel while substantially continually increasing the pressurization fluid flowrate into the vessel and maintaining the pressurization fluid velocity within plus or minus 25 percent.

20. The method of claim 16 wherein the pressurization fluid is nitrogen.

21. The method of claim 16 wherein the target pressure is within the range of from 105 to 150 percent of the service pressure of the vessel.

22. The method of claim 16 wherein the pressure vessel is a gas storage cylinder.

23. The method of claim 16 wherein the pressure vessel is a tube trailer.

24. The method of claim 18 wherein the pressurization fluid flowrate is increased at least once during step (d).

* * * * *